(12) United States Patent
Perego et al.

(10) Patent No.: US 6,642,172 B1
(45) Date of Patent: *Nov. 4, 2003

(54) EXTRUDED CATALYST BASED ON SILICA/ALUMINA GEL

(75) Inventors: Carlo Perego, Milan (IT); Gianluca Bassi, Milan (IT); Gianni Girotti, Bologna (IT)

(73) Assignees: Eniricerche S.p.A., San Donato Milanese (IT); Agip Petroli S.p.A., Rome (IT); Enichem Synthesis S.p.A., Palermo (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/377,829

(22) Filed: Jan. 25, 1995

(30) Foreign Application Priority Data

Jan. 28, 1994 (IT) .......................................... MI94A0142

(51) Int. Cl.⁷ ................................................ B01J 21/12

(52) U.S. Cl. ........................................ 502/235; 502/263

(58) Field of Search ................................. 502/235, 263; 501/12, 68, 55, 73

(56) References Cited

U.S. PATENT DOCUMENTS

| | | | |
|---|---|---|---|
| 5,049,536 A | * 9/1991 | Bellussi et al. | 502/235 |
| 5,051,386 A | * 9/1991 | Ward et al. | 502/64 |
| 5,342,814 A | 8/1994 | Peratello et al. | 502/263 |
| 5,348,924 A | * 9/1994 | Potter et al. | 502/69 |

FOREIGN PATENT DOCUMENTS

| | | |
|---|---|---|
| EP | 0 309 139 | 3/1989 |
| EP | 0 340 868 | 11/1989 |
| EP | 0 550 922 | 7/1993 |

* cited by examiner

*Primary Examiner*—Stuart L. Hendrickson
(74) *Attorney, Agent, or Firm*—Oblon, Spivak, McClelland, Maier & Neustadt, P.C.

(57) ABSTRACT

A catalyst in the form of extruded bodies is disclosed, which consists of an inert binding agent and a catalytically active phase of a silica/alumina gel. The catalyst is particularly active in acid-catalysed reactions.

8 Claims, 1 Drawing Sheet

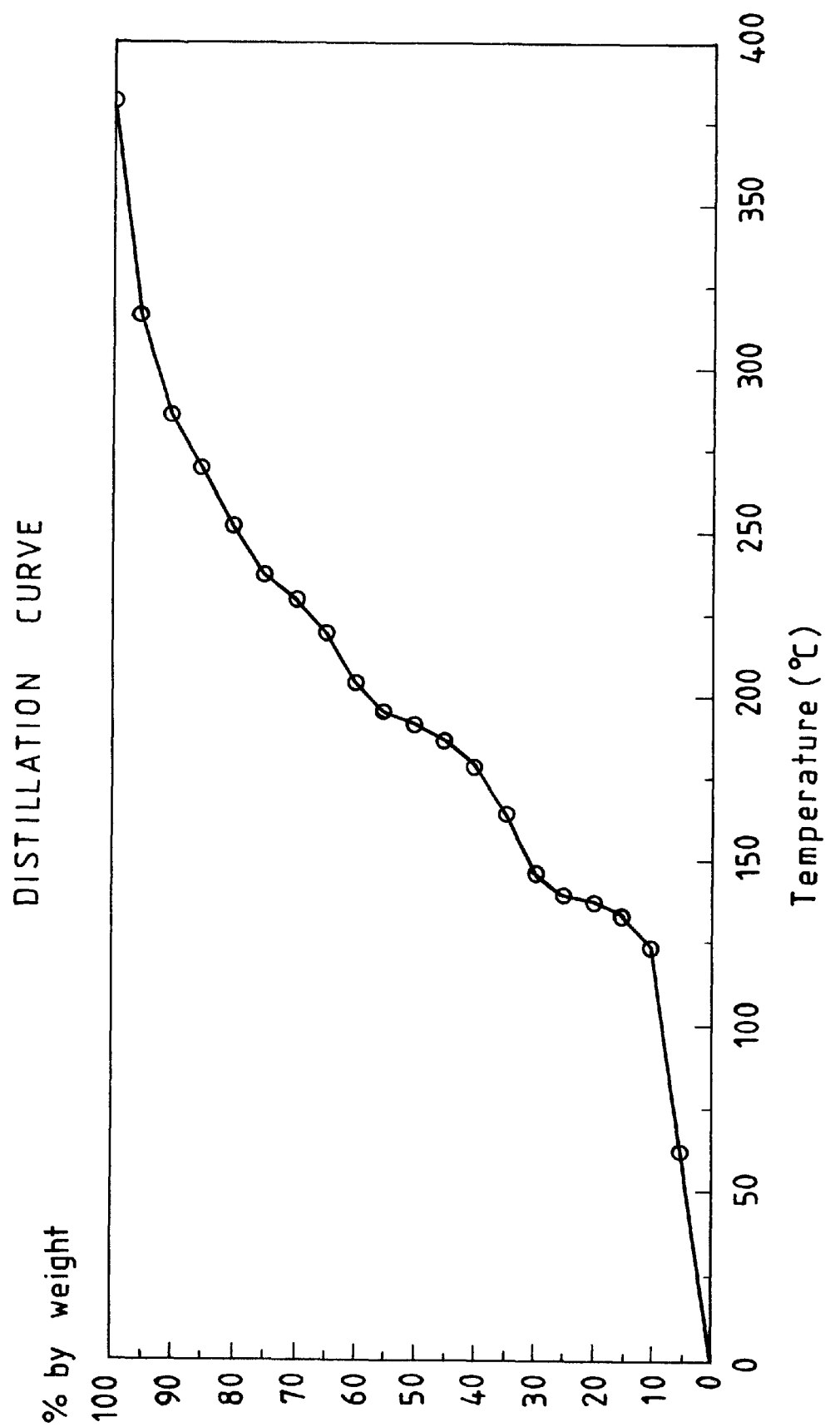

EXTRUDED CATALYST BASED ON SILICA/ALUMINA GEL

The present invention relates to a catalyst in extruded form which is obtained by mixing a high-viscosity sol obtained from the hydrolysis and polycondensation of silicates and aluminates, with an inert binding agent.

The invention relates as well to the use of such a catalyst in olefin oligomerization processes.

Some silica/alumina gels, of amorphous character, displaying catalytic activity, are known in the art. So, e.g., in EP 160,145 a process for alkylating aromatic hydrocarbons is disclosed, which uses a catalyst consisting of a silica/alumina gel, of amorphous character, having pores with a diameter typically comprised within the range of from 50 to 500 Ångstroms, and with a ratio of silica to alumina typically, comprised within the range of from 1:1 to 10:1.

M. R. S. Manton and J. Davidtz in Journal of Catalysis, 60, 156–166 (1979) describe a process for the synthesis of amorphous silica/alumina catalysts having a controlled pore volume, i.e., typically comprised within the range of from 3.7 to 15 nm.

European patent application EP 340,868 discloses a silica/alumina gel, amorphous when examined by X-ray analysis, having a molar ratio of $SiO_2/Al_2O_3$ of from 30:1 to 500:1, with a specific surface area comprised within the range of from 500 to 1000 $m^2/g$, a total pore volume of from 0.3 to 0.6 ml/g, and substantially free from pores with larger diameter than 30 Ångstroms.

This silica-alumina gel is prepared as follows:

(a) an aqueous solution is prepared of a tetraalkyl ammonium hydroxide (TAA—OH), a soluble aluminum compound capable of yielding $Al_2O_3$ by hydrolysis and a silicon compound capable of yielding $SiO_2$ by hydrolysis, in the following mutual molar ratios:

$$SiO_2 : Al_2O_3 = \text{from } 30:1 \text{ to } 500:1$$

$$TAA\text{—}OH : SiO_2 = \text{from } 0.05:1 \text{ to } 0.2:1$$

$$H_2O : SiO_2 = \text{from } 5:1 \text{ to } 40:1;$$

(b) the resulting solution is heated in order to cause it to undergo hydrolysis and gelation;
(c) the resulting gel is dried;
(d) the dried gel is calcined, firstly under an inert atmosphere and then under an oxidizing atmosphere.

The resulting silica/alumina gel is catalytically active in hydrocarbon conversion processes.

Of course, the problem existed of rendering the silica/alumina gel disclosed in the above said patent application best suitable for industrial use, by endowing it with adequate properties of mechanical strength, without endangering the high catalytic performance thereof.

Those skilled in the art are aware of the possible procedures for preparing extruded bodies having high enough mechanical strength values, without altering their catalytic performance. Thus, for example, the catalyst can be ground, so as to obtain powders consisting of particles with a suitable size, which are subsequently blended with a thickener.

A further preparation method consists in blending silica/alumina gel powders with a second powder of a metal oxide in the presence of a thickening agent.

All these techniques yield extrudates endowed with good mechanical strength and unchanged catalytic performance.

In EP 550,922 an extruded catalyst is disclosed which is prepared according to known techniques, and consists of:

a catalytically active portion constituted by the silica/alumina gel disclosed in EP 340,868;
an inert binding agent constituted by aluminas belonging to the class of boehmite or pseudo-boehmite.

This catalyst displays a good mechanical strength, and results to be more active than pristine silica/alumina gel.

Said catalyst is prepared by blending the catalytically active portion constituted by silica/alumina gel, suitably ground in order to obtain a powder with a smaller average diameter than 50 microns, with the inert binding agent, in the presence of a thickener containing a mineral or organic acid, until a homogeneous paste is obtained which is then extruded yielding small cylindrical bodies of catalyst which are submitted to ageing, drying at 100–120° C. and calcination in air at a temperature comprised within the range of from 500 to 600° C.

The present Applicants found now unexpectedly, that by adding boehmite or pseudo-boehmite during that silica/alumina gel preparation step which precedes the drying and calcination steps, a catalyst is obtained which is more active than pristine gel, and the extruded catalyst disclosed in EP 550,922, based on a silica/alumina gel and a binding agent selected from boehmite or pseudo-bohemite.

Furthermore, the catalyst according to the present invention requires a lower number of synthesis steps than as required in order to prepare the extruded catalyst of EP 550,922: in particular, the step of grinding the dried/calcined gel is no longer necessary, and the drying and calcination steps are carried out once only, on the extruded catalyst.

Therefore, the object of the present invention is a catalyst in extruded form, consisting of an inert binder agent and a catalytically active portion of silica/alumina gel, which is obtained by:

(a) preparing an aqueous solution of a tetraalkyl ammonium hydroxide (TAA—OH), a soluble aluminum compound capable of yielding $Al_2O_3$ by hydrolysis and a silicon compound capable of yielding $SiO_2$ by hydrolysis, in the following mutual molar ratios:

$$SiO_2 : Al_2O_3 = \text{from } 30:1 \text{ to } 500:1$$

$$TAA\text{—}OH : SiO_2 = \text{from } 0.05:1 \text{ to } 0.2:1$$

$$H_2O : SiO_2 = \text{from } 5:1 \text{ to } 40:1;$$

(b) heating the resulting solution in order to cause the reaction mixture to undergo hydrolysis and gelation, and obtain an (A) mixture having a viscosity comprised within the range of from 0.01 to 100 Pa·sec;
(c) adding to said (A) mixture, firstly a binding agent selected from the class of boehmites or of pseudo-boehmites, in a ratio, by weight, to said (A) mixture comprised within the range of from 0.05 to 0.5; and then a mineral or organic acid, in an amount comprised within the range of from 0.5 to 8 g per 100 g of binding agent;
(d) mixing and heating up to a temperature comprised within the range of from 40 to 90° C., the resulting mixture from above (c) step, until a homogeneous paste is obtained, which is submitted to extrusion;
(e) the resulting extrudate is dried;
(f) the dried extrudate is calcined under an oxidizing atmosphere.

The composition of the mixture from the (a) step and the nature of the reactants used are in accordance with the teachings of EP 340,868.

The (b) step is carried out at a temperature comprised within the range of from 60 to 100° C., during a time comprised within the range of from 15 minutes to 2 hours. Reaching a viscosity of from 0.01 to 100 Pa·sec is critical in this step. More viscous, or less viscous products are unsuitable for those treatments according to the subsequent processing steps.

In the (c) step, the binding agent is preferably used in powder form, with an average particle diameter of less than 50 μm.

According to a preferred aspect of the present invention, in the (c) step also a plasticizer is added. The plasticizer can be, e.g., methyl cellulose, stearin, glycerol. The plasticizer is added at an intermediate time between the addition of the binding agent and the addition of mineral or organic acid.

In the (d) step, the mechanical mixing and heating cause the solvent to evaporate until a homogeneous paste is obtained which has such a consistency as normally regarded as suitable for the extrusion. Cylindical catalyst bodies are obtained with sizes which may be varied as a function of application requirements, and are then submitted to ageing at a temperature comprised within the range of from 20 to 40° C.

In the (e) step, the catalyst is submitted to an oven-drying at 100–120° C., and then, in the (f) step, to a calcination in air, at a temperature comprised within the range of from 500 to 600° C.

The resulting catalyst has a higher catalytic activity than pristine silica/alumina gel, as well as than silica/alumina gel bound, according to the well-known methods, with bohemite or pseudo-bohemite.

This catalyst is furthermore well useable at an industrial level, because it displays an axial breaking strength comprised within the range of from 25 to 280 kg/cm$^2$, a bimodal porosity distribution and a specific surface area comprised within the range of from 400 to 600 m$^2$/g.

The catalyst of the present invention can be suitably used in the usual acid-catalysed petrochemical reactions, as alkylation, isomerization and oligomerization.

In particular, it is very effective in the reaction of oligomerization of light olefins, in particular propylene, to yield hydrocarbon cuts displaying extremely good properties as gasoline and jet fuel.

Said oligomerization is suitably carried out at a temperature comprised within the range of from 100 to 250° C. and under a pressure of from 10 to 70 bars.

The following experimental examples are reported in order to better illustrate the invention.

EXAMPLE 1

Catalyst Preparation

An amount of 12 g of aluminum tripropoxide is added to 205 g of tetra-n-propylammonium hydroxide (TPA—OH) at 13.35% by weight; 389 g of demineralized water is then added. The resulting solution is heated up to 60° C. until aluminum compound is completely dissolved; 306 g of tetraethyl silicate is then added with stirring.

The resulting mixture displays the following molar ratios:

$SiO_2 : Al_2O_3 = 50$ $TPA—OH : SiO_2 = 0.09$ $H_2O : SiO_2 = 21.$

The temperature is kept at 60–65° C. until an (A) mixture is obtained with a viscosity of 0.011 Pa·sec.

Eight hundred g of this mixture, after a 20-hour ageing at room temperature, is charged to a mixer and then 80 g of pseudo-boehmite VERSAL 150 (ex La Roche) and 13 g of methyl cellulose (Methocel 64625 ex Fluka) are added. After about a 1-hour mixing, 1.6 g of glacial acetic acid is added and the temperature of the jacket of the kneader is increased up to about 50–60° C. Kneading is continued of the mixture while hot, until a homogeneous paste is obtained with a suitable consistency for extrusion.

After the extrusion, the resulting extrudate is aged overnight at room temperature, the aged extrudate is dried at 100° C. during 5 hours and the dried extrudate is submitted to a 8-hour calcination at 550° C. in air.

A catalyst is obtained which displays a mechanical axial strength of 249 kg/cm$^2$ and a specific surface area of 608 m$^2$/g.

EXAMPLE 2

Catalyst Preparation

An (A) mixture is prepared as disclosed in above Example 1.

An amount of 500 g of this mixture is charged to a mixer and then 115 g of pseudo-boehmite VERSAL 150 (ex La Roche) and 19 g of methyl cellulose (Methocel 64625 ex Fluka) are added to the mixer. After an about 1-hour mixing, 0.6 g of glacial acetic acid is added and the temperature of the jacket of the kneader is increased up to about 50–60° C. Kneading is continued of the mixture while hot, until a homogeneous paste is obtained with a suitable consistency for extrusion.

After the extrusion, the resulting extrudate is aged overnight at room temperature, the aged extrudate is dried at 100° C. during 5 hours and the dried extrudate is submitted to a 8-hour calcination at 550° C. in air. A catalyst is obtained which displays a mechanical axial strength of 278 kg/cm$^2$ and a specific surface area of 500 m$^2$/g.

EXAMPLE 3

Catalyst Preparation

The process is carried out as in Example 2, without adding methyl cellulose and using 2.3 g of glacial acetic acid.

A catalyst is obtained which displays a mechanical axial strength of 25 kg/cm$^2$ and a specific surface area of 485 m$^2$/g.

EXAMPLE 4

Catalyst Preparation

The process is carried out as in Example 3, using 5 g of glacial acetic acid dissolved in 10 ml of water.

A catalyst is obtained which displays a mechanical axial strength of 99 kg/cm$^2$ and a specific surface area of 500 m$^2$/g.

EXAMPLE 5

Reference Catalyst Preparation

An amount of 12 g of aluminum tripropoxide is added to 205 g of tetra-n-propylammonium hydroxide (TPA—OH) at 13.35% by weight; 389 g of demineralized water is then added. The resulting solution is heated up to 60° C. until aluminum compound is completely dissolved; 306 g of tetraethyl silicate is then added with stirring.

The resulting mixture displays the following molar ratios:

$$SiO_2 : Al_2O_3 = 50$$

$$TPA\text{---}OH : SiO_2 = 0.09$$

$$H_2O : SiO_2 = 21.$$

The temperature is kept at 60–65° C. during a 60-minute time. The resulting gel is caused to age for 10 hours at room temperature, is then dried for 3 hours on the Rotavapor Rotary Evaporator, under a flowing air stream, then in an oven at 100° C. After an 8-hour calcination at 550° C., a silica/alumina gel is obtained with a ratio of $SiO_2:Al_2O_3$ of 50, a surface area of 672 m²/g and a porosity of 0.454 ml/g.

100 g of this silica/alumina gel is ground within a Rotary Drum Mill until a powder with an average distribution of particle size comprised within the range of from 10 to 200 microns is obtained. To such a powder, 100 g of a commercial pseudo-boehmite (CATAPAL B—VISTA CHEMICAL COMPANY) is added. Both powders are mechanical mixed on the kneader, during 10 minutes.

Separately, an aqueous solution of methyl-cellulose at 1% by weight is prepared and 130 g of this solution is then acidified with 2 g of glacial acetic acid (at 99.8% by weight).

The acidified aqueous methylcellulose solution is then added to the powder blend and mixing is continued until a homogeneous paste is obtained.

The so obtained paste is extruded and the resulting extrudate is then submitted to an overnight ageing at room temperature. The aged extrudate is dried at 100° C. for 5 hours, and is calcined at 550° C. for 8 hours in air.

At the end of this process, a catalyst is obtained which shows a mechanical axial strength of 87 kg/cm and of a specific surface area of 482 m²/g.

EXAMPLE 6

Propylene Oligomerization

The extruded catalyst obtained as disclosed in Example 1 was tested in the reaction of propylene oligomerization under the following operating conditions:

catalyst shape: cylindrical extruded body;
catalyst size: average diameter of approximately 2.7 mm, average length of approximately 5 mm;
reactor type: fixed-bed reactor;
reactor size: inner diameter of 25.4 mm, length of 700 mm;
feed: 70:30 propylene/propane mixture;
reactor temperature: 120° C.;
reactor pressure: 35 bars;
space velocity WHSV: 1 and 1.76 g of propylene per gram of active phase per hour.

The results obtained from these tests are reported in Table 1, in which T.O.S. (time on stream) is the total test time:

TABLE 1

| WHSV (h⁻¹) | Pressure (bars) | Temp. (° C.) | T.O.S. | Convers. rate (%) |
|---|---|---|---|---|
| 1 | 35 | 120 | 17 | 96 |
| 1 | 35 | 120 | 28 | 96 |
| 1 | 35 | 120 | 45 | 96 |

TABLE 1-continued

| WHSV (h⁻¹) | Pressure (bars) | Temp. (° C.) | T.O.S. | Convers. rate (%) |
|---|---|---|---|---|
| 1.76 | 35 | 120 | 51 | 91 |
| 1.76 | 35 | 120 | 69 | 90 |

EXAMPLE 7

The catalyst obtained according to Example 3 was tested in the reaction of propylene oligomerization under similar operating conditions as of Example 6, except for temperature and WHSV:

reactor temperature: comprised within the range of from 120° C. to 160° C.;
space velocity WHSV: 1.85 g of propylene per gram of active phase per hour.

The results obtained from these tests are reported in Table 2:

TABLE 2

| WHSV (h⁻¹) | Pressure (bars) | Temp. (° C.) | T.O.S. | Convers. rate (%) |
|---|---|---|---|---|
| 1.85 | 35 | 120 | 15 | 82 |
| 1.85 | 35 | 130 | 38 | 80 |
| 1.85 | 35 | 140 | 62 | 82 |
| 1.85 | 35 | 160 | 133 | 86 |
| 1.85 | 35 | 160 | 210 | 84 |

EXAMPLE 8

The catalyst obtained according to Example 4 was tested in the reaction of propylene oligomerization under similar operating conditions as of Example 6, except for temperature:

reactor temperature: comprised within the range of from 120° C. to 200° C.

The results obtained from these tests are reported in Table 3:

TABLE 3

| WHSV (h⁻¹) | Pressure (bars) | Temp. (° C.) | T.O.S. | Convers. rate (%) |
|---|---|---|---|---|
| 1.85 | 35 | 120 | 22 | 91 |
| 1.85 | 35 | 130 | 44 | 92 |
| 1.85 | 35 | 140 | 67 | 93 |
| 1.85 | 35 | 160 | 138 | 92 |
| 1.85 | 35 | 170 | 163 | 92 |
| 1.85 | 35 | 180 | 185 | 92 |
| 1.85 | 35 | 190 | 208 | 92 |
| 1.85 | 35 | 200 | 230 | 93 |

The product obtained by operating under such conditions as summarized in Table 3, first line, contains a suitable fraction for use as gasolines (boiling temperature comprised within the range of from 60 to 175° C.), and a suitable fraction for use as jet fuel (boiling temperature comprised within the range of from 175 to 300° C.).

The distillation curve of said product is reported in the single accompanying FIGURE.

EXAMPLE 9

COMPARISON EXAMPLE

The catalyst obtained as disclosed in Example 5 was tested in the reaction of propylene oligomerization under the following operating conditions:

catalyst shape: cylindrical extruded body;
catalyst size: average diameter of approximately 2.7 mm, average length of approximately 5 mm;
reactor type: fixed-bed reactor;
reactor size: inner diameter of 25.4 mm, length of 700 mm;
feed: 70:30 propylene/propane mixture;
reactor temperature: comprised within the range of from 120° C. to 200° C.;
inner reactor pressure: 38 bars;
space velocity WHSV: from 1.8 to 3.1 g of propylene per gram of active phase per hour.

The results obtained from these tests are reported in following Table 4:

TABLE 4

| WHSV ($h^{-1}$) | Pressure (bars) | Temp. (° C.) | T.O.S. | Convers. rate (%) |
|---|---|---|---|---|
| 1.8 | 38 | 120 | 24 | 73 |
| 2.7 | 38 | 160 | 139 | 81 |
| 3.1 | 38 | 160 | 204 | 58 |
| 2.2 | 38 | 200 | 480 | 55 |

What is claimed is:

1. An extruded catalyst consisting of:
a catalytically active portion of silica/alumina gel having a silica/alumina molar ratio ranging from 50:1 to 500:1 and an inert binding agent, which is prepared by:
   (a) preparing an aqueous solution of a tetraalkylammonium hydroxide (TAA—OH), a soluble aluminum compound capable of yielding $Al_2O_3$ by hydrolysis and a silicon compound capable of yielding $SiO_2$ by hydrolysis, in the following molar ratios:
   $SiO_2:Al_2O_3$=from 50:1 to 500:1
   TAA—OH:$SiO_2$=from 0.05:1 to 0.2:1
   $H_2O:SiO_2$=from 5:1 to 40:1;
   (b) heating the resulting solution (a) in order to effect hydrolysis and gelation of the components of solution (a) thereby obtaining mixture (A) having a viscosity within the range of from 0.01 to 100 Pa sec;
   (c) adding to said mixture (A), firstly a binding agent selected from the group consisting of a boehmite and a pseudo-boehmite, in a ratio, by weight, to said mixture (A) within the range of from 0.05 to 0.5, followed by a plasticizer, and then adding an organic acid in an amount within the range of from 0.5 to 8 g per 100 g of binding agent;
   (d) mixing the combined material of step (c) and heating the mixture to a temperature within the range of from 40 to 90° C. until a homogeneous paste is obtained;
   (e) extruding said paste;
   (f) drying the extrudate; and
   (g) calcining the dried extrudate under an oxidizing atmosphere, wherein the axial breaking strength of the catalyst ranges from 99 kg/cm$^2$ to 280 kg/cm$^2$.

2. The catalyst according to claim 1, wherein said plasticizer is methyl lose, stearin or glycerol.

3. The catalyst according to claim 1, wherein step (b) is conducted at a temperature within the range of from 60 to 100° C. during a time within the range of from 15 minutes to 2 hours.

4. The catalyst according to claim 1, wherein the binding agent of step (c) is in powder form whose particles have an average diameter of less than 50 μm.

5. The catalyst according to claim 1, wherein the drying of step (f) is conducted at a temperature within range of from 100 to 120° C.

6. The catalyst according to claim 1, wherein the calcination of step (g) is conducted at a temperature within the range of from 500 to 600° C.

7. The catalyst according to claim 1, which has an axial breaking strength of from 25 to 280 kg/cm$^2$, a bimodal porosity distribution and a specific surface area within the range of from 400 to 600 m$^2$/g.

8. A process of preparing an extruded catalyst consisting of a catalytically active portion of silica/alumina gel having a silica/alumina molar ratio ranging from 50:1 to 500:1 dispersed in an inert binder agent, which is obtained by:
   (a) preparing an aqueous solution of a tetraalkylammonium hydroxide (TAA—OH), a soluble aluminum compound capable of yielding $Al_2O_3$ by hydrolysis and a silicon compound capable of yielding $SiO_2$ by hydrolysis, in the following mutual molar ratios:
   $SiO_2:Al_2O_3$=from 50:1 to 500:1
   TAA—OH:$SiO_2$=from 0.05:1 to 0.2:1
   $H_2O:SiO_2$ from 5:1 to 40:1;
   (b) heating the resulting solution (a) in order to effect hydrolysis and gelation of the components of solution (a) thereby obtaining mixture (A) having a viscosity within the range of from 0.01 to 100 Pa sec;
   (c) adding to said mixture (A), firstly a binding agent selected from the group consisting of a boehmite and a pseudo-boehmite, in a ratio, by weight, to said mixture (A) within the range of from 0.05 to 0.5, followed by a plasticizer, and then adding an organic acid in an amount within the range of from 0.5 to 8 g per 100 g of binding agent;
   (d) mixing the combined material of step (c) and heating the mixture to a temperature within the range of from 40 to 90° C. until a homogeneous paste is obtained;
   (e) extruding said paste;
   (f) drying the extrudate; and
   (g) calcining the dried extrudate under an oxidizing atmosphere, wherein the axial breaking strength of the catalyst ranges from 99 kg/cm$^2$ to 280 kg/cm$^2$.

* * * * *